United States Patent [19]

Widder

[11] Patent Number: 4,675,173

[45] Date of Patent: Jun. 23, 1987

[54] METHOD OF MAGNETIC RESONANCE IMAGING OF THE LIVER AND SPLEEN

[75] Inventor: Kenneth J. Widder, Del Mar, Calif.

[73] Assignee: Molecular Biosystems, Inc., San Diego, Calif.

[21] Appl. No.: 732,173

[22] Filed: May 8, 1985

[51] Int. Cl.$^4$ .................. A61K 49/00; A61B 5/05; A61B 6/00

[52] U.S. Cl. .................................... 424/9; 128/653; 128/654; 436/173; 436/526; 436/806; 252/62.51

[58] Field of Search .................... 424/9; 128/653, 654; 436/526, 173, 806; 252/62.51

[56] References Cited

U.S. PATENT DOCUMENTS

| | | |
|---|---|---|
| 4,247,406 | 1/1981 | Widder et al. |
| 4,452,773 | 6/1984 | Molday .................. 424/1.1 |
| 4,615,879 | 10/1986 | Runge et al. .................. 436/806 X |

FOREIGN PATENT DOCUMENTS 2137612  10/1984  United Kingdom .

OTHER PUBLICATIONS

Wesby et al., Radiology (1983) 149:175-180.
Runge et al., Radiology (1983) 147:789-791.
Stark et al., Radiology (1983) 148:743-751.
Becker, "High Resolution NMR", (2nd ed., 1980, Academic Press), pp. 48-51.

*Primary Examiner*—Christine M. Nucker
*Assistant Examiner*—Stephen C. Wieder
*Attorney, Agent, or Firm*—Tilton, Fallon, Lungmus & Chestnut

[57] ABSTRACT

A method of magnetic resonance imaging (MRI) of liver and/or spleen is provided employing encapsulated contrast agents in the form of microspheres having a biodegradeable matrix with the paramagnetic/ferromagnetic contrast agent dispersed therein. Ferromagnetic contrast agents such as magnetite are preferred. Ferromagnetic microspheres when administered intravenously segregate through the reticuloendothelial system in the liver and spleen where they reduce the $T_2$ relaxation time to obtain improved MR imaging.

14 Claims, No Drawings

METHOD OF MAGNETIC RESONANCE IMAGING OF THE LIVER AND SPLEEN

FIELD OF INVENTION, BACKGROUND, AND PRIOR ART

The field of this invention relates to magnetic resonance (MR) imaging (MRI) of the human body and to the use of paramagnetic contrast agents to improve the diagnostic usefulness of the MR images. More particularly, this invention is concerned with a method of MRI examintion of the liver and spleen.

MR imaging of the human body can display both normal anatomy and a variety of organ pathologies, including tumors. For example, the liver, pancreas, spleen, and gall bladder can be imaged by tomographic slices in various planes. The techniques used for MRI liver examination have included delineation by spine-cho, inversion recovery, and saturation recovery pulse sequences but definition of normal from abnormal has not been predictable. In hepatic MRI, specifically, contrast resolution of the hepatic images varies greatly depending on the data acquisition technique employed to obtain the image, although tumors associated with the liver or spleen usually result in prolongation of both the longitudinal ($T_1$) and the transverse ($T_2$) relaxation times as compared with normal tissues. Earlier reports have emphasized the importance of using paramagnetic agents to increase the $T_1$ differences between normal and pathologic tissues and considered coincidental $T_2$ diminution an impediment.

Paramagnetic contrast agents as free metal ions, chelates, or insoluble metal compounds have been described for use in enhancing intrinsic contrast in MR imaging. Such paramagnetic metals include gadolinium, chromium, copper, manganese, and iron. Because of possible toxicity, soluble chelates have been suggested for parenteral administration and insolubilized compounds for oral administration. Heretofore, however, the targeting of stable contrast agents to the liver and spleen has not been satisfactory.

An effective, safe reticuloendothelial system (RES) MRI contrast agent which can increase the sensitivity and differentiation of normal and pathologic tissue in the liver or spleen has not been previously described. This problem is aggravated by the fact that existing modalities for other imaging procedures for the liver and spleen have approximately a 10-20% false-negative rate for detecting hepatic metastases, and a 40-50% false-negative rate for detecting lymphomatous involvement, necessitating laproscopic staging. Further, as pointed out above, tumor involvement of liver, spleen and other tissues has consistently been shown to increase $T_1$ and $T_2$ relaxation parameters to a variable and unpredictable degree, which also results in a high incidence of false-negatives. RES agents are useful because liver replaced by tumor does not possess RES cells and therefore does not take up the contrast agent. Non-RES agents more randomly distribute between normal and pathologic tissue.

Hepatic disease conditions resulting in abnormally high levels of iron in the liver have been shown to produce alterations of tissue relaxation times as observed by MRI. See, for example, Doyle, et al., *Am. J. Roentgenol.* (1982) 138: 193-200; Stark, et al., *Radiology* (1983) 148: 743-751; and Runge, et al., *Am. J. Roentgenol.* (1983) 141: 943-948. Observed decreases in $T_1$ have been attributed either to paramagnetic enhancement of longitudinal relaxation, or to alterations of hydrated tissue proteins. Heretofore, the production of $T_2$ diminution as seen in these disease states has not been produced with a potent, safe contrast agent. Soluble iron compounds have been tested as MRI contrast agents. Wesbey, et al., *Radiology* (1983) 149: 175-180.

SUMMARY OF INVENTION

The method of the present invention for MRI examination of the liver and/or spleen utilizes encapsulated paramagnetic contrast agents in the form of critically sized microspheres. Preferably, the contrast agents are ferromagnetic as well as paramagnetic. By utilizing microspheres within the size range of 1.5 to 8 microns, such as 2 to 5 microns, the parenterally administered contrast agents are rapidly segregated by the reticuloendothelial system and concentrated in the liver and spleen. Effective segregation and concentration in these organs can occur in as short a time as 1 to 10 minutes. Only a small quantity of the microspheres needs to be administered for effective reduction of the $T_2$ relaxation time of the subject's liver and/or spleen. The method emphasizes $T_2$ differences between normal and pathological tissues, improving visual contrast without losing anatomical detail.

Because of the effectiveness of the targeting to the liver and spleen, toxicity reactions and other side effects are minimized. Further, the contrast agent may be selected for use in a form providing reduced toxicity, such as chelated or stable insolubilized forms of paramagnetic metals. Particularly effective results can be obtained with iron compounds at doses which are highly tolerated in the liver and spleen. A preferred form of paramagnetic iron is the magnetic oxide of iron known as magnetite.

The advantages of the encapsulated contrast agents of the present invention for hepatic and splenic imaging include the following: (1) superior targeting as compared with contrast agents that are distributed primarily in the blood pool and interstitium, or metabolized by hepatocytes; (2) the contrast material may be composed of physiologic concentrations of normal physiologic substrate, such as human serum albumin matrix and iron oxides, which can be metabolized, for example, by normal physiologic mechanisms of clearance; (3) toxicity can be minimized by rapid clearance by reticuloendothelial system when administered intravenously which protects the metabolically functional hepatocytes from exposure to the contrast material (viz. the first pass clearance can be approximately 80%); (4) rapid intravenous clearance by the target liver and spleen is predictable with a normal functioning reticuloendothelial system; and (5) the microspheres can be nonembolic in size and need not be trapped by the proximal arteriolar bed. By employing the method of this invention to reduce the transverse relaxation time ($T_2$) in MR imaging of the liver and spleen, tumors may be observed with much greater accuracy and clarity. The concentration in the liver and spleen of the encapsulated contrast agent by "blackening" the normal tissue highlights on areas replaced by tumor.

DETAILED DESCRIPTION

The method of this invention is generally applicable to paramagnetic contrast agents in both soluble and insoluble forms. Preferably, the contrast agent is both paramagnetic and ferromagnetic or hyperparamagnetic.

However, all of the known paramagnetic metals can be employed, including not only iron, which is both paramagnetic and ferromagnetic, but also other paramagnetic metals, such as gadolinium, chromium, copper, manganese, etc.

It is preferred to use the paramagnetic agent in particulate form as submicron size particles, for example, as particles of 50 to 300 Angstroms diameter. Larger particle sizes can be employed providing the particles are small enough for incorporation in microspheres in the size range of 1.5 to 8 microns. Preferably, the particulate forms are substantially water-insoluble, such as insoluble oxides or salts. The paramagnetic agent may also be in the form of particles of the elemental metal.

A preferred substantially water-insoluble particulate contrast agent is magnetite, which is a magnetic iron oxide sometimes represented as $Fe_3O_4$ or more exactly as $FeO.Fe_2O_3$. Commercially, fine powders or suspensions of magnetitue are available from Ferrofluidics Corporation, Burlington, Mass. The size range of the particles is submicron, viz. 50 to 200 Angstroms. Other water-insoluble paramagnetic compounds can be used such as ferrous oxide ($Fe_2O_3$), iron sulfide, iron carbonate, gadolinium oxalate, etc. The contrast agents may also be employed in the form of water-soluble salts or chelates. For example, ferrous or ferric chloride, ferric ammonium citrate, ferrous sulfate heptahydrate, etc. may be used. Other water-soluble salts include manganous chloride, chromium chloride, etc. For the toxic paramagnetic metals, however, it is preferred to employ chelated forms of the metals, such as for example Cr-EDTA (chromium ethylenediaminetetraacetate) or Gd-EDTA. Other chelates of paramagnetic metals are described in the published European Patent Application No. 0 071 564.

For purposes of this invention, the microspheres comprise relatively sperhical particles consisting of protein, carbohydrate or lipid as the biodegradeable matrix for the paramagnetic contrast agent. For effective targeting to the liver and spleen, the microspheres comprising the encapsulated contrast agents should have diameters of at least 1.5 microns and preferably of larger average size up to about a maximum size of 8 microns. An advantageous size range appears to be from about 2 to 5 micron diameter. Less than 1.5 micron microspheres can be used as a liver spleen contrast agent, but circulation time is prolonged so fewer spheres will be rapidly taken up by the RES. Microspheres of larger size than 8 microns may be sequestered in the first capillary bed encountered, and thereby prevented from reaching the liver and spleen at all. Large microspheres (viz. 10 microns or more) can be easily trapped in the lungs by arteriolar and capillary blockade. See Wagner, et al., *J. Clin. Investigation* (1963), 42: 427; and Taplin, et al., *J. Nucl. Medicine* (1964) 5: 259.

The matrix material may be a biodegradeable protein, polysaccharide, or lipid. Non-antigenic proteins are preferred such as, for example, human serum albumin. Other amino acid polymers can be used such as hemoglobin, or synthetic amino acid polymers including poly-L-lysine, and poly-L-glutamic acid. Carbohydrates such as starch and substituted (DEAE and sulfate) dextrans can be used. (See *Methods in Enzymology*, 1985, Vol. 112, pages 119–128). Lipids useful in this invention include lecithin, cholesterol, and various charged phospholipids (stearyl amines or phosphatidic acid).

Microspheres for use in practicing the method of this invention can be prepared from albumin, hemoglobin, or other similar amino acid polymers by procedures heretofore described in literature and patent references. See, for example, Kramer, *J. Pharm. Sci.* (1974) 63: 646; Widder, et al., *J. Pharm, Sci.* (1979) 68: 79; Widder and Senyei, U.S. Pat. No. 4,247,406; and Senyei and Widder, U.S. Pat. No. 4,230,685.

Briefly, an aqueous solution is prepared of the protein matrix material and the paramagnetic/ferromagnetic contrast agent, and the aqueous mixture is emulsified with a vegetable oil, being dispersed droplets in the desired microsphere size range. Emulsification can be carried out at a low temperature, such as a temperature in the range of 20°–30° C., and the emulsion is then added dropwise to a heated body of the same oil. The temperature of the oil may range from 70° to 160° C. The dispersed droplets in the heated oil are hardened and stabilized to provide the microspheres which are then recovered. When most of the microspheres as prepared, such as 80% or more, have sizes within the ranges described above, they can be used as prepared. However, where substantial amounts of oversized or undersized microspheres are present, such as over 10 to 20% of microspheres larger than 8 microns, or over 10 to 20% of microspheres smaller than 1.5 microns, a size separation is desirable. By the use of a series of micropore filters of selective sizes, the oversized and undersized microspheres can be separated and the microspheres of the desired size range obtained.

The microspheres may contain from 5 to 100 parts by weight of the contrast agent per 100 parts of the matrix material. For example, in preferred embodiments, microspheres can contain from 10 to 30 parts by weight of magnetite particles or another contrast agent per 100 parts of matrix material such as serum albumin.

Intravenous parenteral infusion is the preferred administration route for the microspheres. However, selective intra-arterial injection/infusion can be employed. Where the microspheres contain from 10–40 parts by weight of the contrast agent per 100 parts of the matrix material doses within the range from 1 to 40 milligrams per kilogram of body weight of the human subject can be used. For example, typical doses are 5 to 15 mg/kg. With albumin microspheres containing 20% magnetite, the amount administered may comprise 10 mg of the microspheres per kg body weight. For administration, the microspheres may be suspended in a sterile solution of normal saline.

In practicing the method of the inventions, the microspheres containing the contrast agent are parenterally administered prior to the MRI examination. The examination is delayed until the microspheres have been segregated by the reticuloendothelial system and are concentrated in the liver and spleen. A suitable period of delay is from about 1 to 10 minutes. The MRI examination is then carried out in the usual manner to obtain images of the liver and/or spleen. The agent is efficaceous for $T_1$, $T_2$ and mixed $T_1$ and $T_2$ weighted pulse sequences. The $T_2$ and mixed sequences are preferred.

EXPERIMENTAL

The method of this invention was tested on an experimental basis using paramagnetic/ferromagnetic iron albumin microspheres. The materials and methods employed were as follows.

I. Preparation.

A water-in-oil emulsion polymerization method was used to prepare microspheres approximately 2-5 micron diameter consisting of heat-denatured human serum albumin matrix in which $Fe_3O_4$, 150-250 Angstrom in size is embedded. In the experiments described below, the following preparation was used. An aqueous solution of 215 mg human serum albumin, 72 mg magnetite in the form of an aqueous suspension (Ferrofluitics Corporation) was made in a volume of 1 ml distilled water. A 0.5 ml aliquot of this suspension was homogenized in 30 ml of cottonseed oil by sonication for one minute. The homogenate was then added dropwise to 100 ml of stirred (1600 RPM) cottonseed oil kept at a constant temperature of 135° C. At ten minutes the emulsion was removed from the heat and stirred until cool. The microspheres were washed free of the oil by centrifugation in anhydrous ether; they were washed free of ether and resuspended in 0.1% Tween 80 and 0.15 normal saline. Microspheres were suspended at a concentration of 10 mg/ml. Prior to use the microsphere suspension was vigorously agitated without sonication. The uniformity of size of the microspheres was checked under the microscope.

II. Rat Imaging Studies.

Magnetic resonance imaging of rats and rabbits was performed with a horizontal bore (8 cm) superconducting magnet system at a magnetic field strength of 1.4 T, corresponding to a $1_H$ resonance frequency of 61.4 MHz. Images were acquired using a two-dimensional Fourier transform technique with slice selection determined by selective irradiation. All images were obtained using 128 phase encoded gradient steps. Reconstructed images (128 × 256 pixels) have a slice thickness of 3 mm and submillimeter in-plane resolution. To enhance T1 contrast, an IR pulse sequence was employed with an echo time of 15 ms; inversion time of 400 ms; and repetition time of 1,460 ms (IR 1,460/400/15).

Fasted (approximately 18 h) male Sprague-Dawley rats (approximately 400 g) were anesthetized with intraperitoneal penobarbital (35 mg/kg) and securely placed on a calibrated carrier and inserted into the magnet. Tubes containing paramagnetically doped water or agar gels of known T1 and T2 were placed alongside the animal. Baseline images were obtained to optimize liver position within the imaging plane.

After baseline images, animals were removed from the magnet and injected with $Fe_3O_4$ albumin microspheres in aqueous suspension at doses of 5-50 mg/microsphere 1,000 g animal weight, into the tail vein. Care was taken not to alter the positioning of the animal during injection and reinsertion into the magnet. Various $T_1$ and $T_2$ weighted pulse sequences were utilized. Imaging was begun immediately and continued for 1.5 to 3 h initially. Rats were subsequently imaged at 18 hrs, 1 month and 3 months.

III. Rat Biodistribution Studies.

A group of 100-200 g male Sprague-Dawley rats, fasted for approximately 18 h, were anesthetized with intraperitoneal pentobarbital (35 mg/kg) and injected with serial concentrations of magnetite-albumin microspheres through a tail vein. At 30 min, the animals were killed by cervical dislocation and tissues obtained for T1 and T2 analyses. Samples included blood (obtained by cardiac puncture), liver, spleen, kidney and thigh muscle (obtained by excision). In all samples T1 and T2 were obtained within 45 min. of death.

All T1 and T2 relaxation measurements were performed with an IBM PC-20 Minispec pulse NMR spectrometer (IBM, Danbury, CT, U.S.A.). This permanent magnet has a field strength of 0.47 T, corresponding to a $^1H$ responance frequency of 20 MHz and operating at 38° C. A microprocessor provided automatic calculation of $T_1$ and $T_2$.

IV. Rabbit VX2 Model.

VX2 carcinoma was implanted in livers of New Zealand white rabbits weighing 800 to 1500 g. by direct laparoscopic intrahepatic implantation. This tumor reaches approximately 1 cm in size and creates nodular metastases within the liver during the first three weeks after implantation.

Tumor bearing animals and controls were studied to determine the biodistribution of the magnetite albumin microspheres, 30 min. post infusion. Animals were sacrified and liver sections obtained to demonstrate histologic correlation with imaging findings, measure the water content of the VX2 metastases and surrounding normal liver and to determine relaxation times $T_1$ and $T_2$ in vitro. Water content was measured by weighing specimens to a constant weight at 60°. In vitro spectroscopy was performed in the IBM PC-20 spectrometer. Liver, tumor, spleen, muscle and blood were studied.

RESULTS

1. Biodistribution of $Fe_3O_4$ Albumin Microspheres

There is a near linear increase in splenic $T_2$ relaxivity ($R_2$) with dose, peaking at approximately 50 mg microspheres/Kg body weight with a 79% increase in $T_2$ relaxivity ($R_2$) and no significant change in $T_1$. At a dose of 10 mg/Kg, there is a 41% increase in splenic $T_2$ relaxivity ($R_2$) with no change in $T_1$. There is a 60% increase in $T_2$ relaxivity ($R_2$) of normal liver at doses of 10-20 mg microspheres and a 16% increase in $T_1$ relaxivity ($R_2$). At 30 minutes post injection of microspheres there is no evidence of microspheres in the intravascular space with no change in blood and renal $T_1$ and $T_2$ parameters.

Peak hepatic (and splenic) paramagnetic effect are seen within five minutes post infusion based on subjective imaging criteria. There is predicted 50-80% first pass clearance of particles this size with 40-70% hepatic and 25-55% splenic uptake. A small percentage is taken up by bone marrow and pulmonary macrophages. The ultimate fate of paramagnetic/ferromagnetic albumin microspheres is not known. Several weeks post infusion of a dose of 10 mg/microspheres/Kg body weight there is persistent diminution of hepatic $T_2$ but there is only a mild to moderate decrease in $T_2$ at 3 months. This probably reflects the normal splenic and hepatic RES turnover which is estimated as 2-3 months in the rat, and is unknown in humans.

2. Rabbit Tumor Model.

Using a VX2 tumor model, a 65% reduction in $T_2$ and a 42% reduction in $T_1$ of normal liver is seen on spectroscopic analysis post infusion of 10 mg of $Fe_3O_4$ albumin microspheres/Kg. There is a 13% reduction of $T_2$ of VX2 tumor at its margin and a 3% reduction of $T_1$, presumably representing small patches of unreplaced normal parenchyma insinuated in tumor. At the tumor margin there is a 53% increase in the difference between normal and pathologic tissue $T_2$ values at the tumor margin and a 39% increase in the difference of $T_1$ values at the tumor margin measured c spectroscopy. Subjectively, the anatomic margins of normal and pathologic tissues became more distinct, as did the true margin of liver, abdominal wall and adjacent viscera, and small areas of tumor involvement became more apparent. This increase in contrast was evident on shorter TR, TE and mixed $T_1$ and $T_2$ pulse sequences with a single average. There was no apparent loss of normal anatomic detail post infusion.

DISCUSSION

A. Toxicity/Fe Overload.

The Fe content of normal human liver is 0.15+0.02 mg Fe/g liver wet weight. The extrapolated adult dosage of microspheres, based on 10 mg/Kg microsphere body weight is 700 mg of microspheres for an average 70 Kg adult, or 140 mg of magnetite (20% of microsphere weight). With an average liver weight of 2200 g (range of approximately 1700-2800 g) and 70% deposition in liver RES (98 mg, $Fe_3O_4$), an average single dose would transiently increase total hepatic Fe by, 0.044 mg/g liver. There is more than a 20 fold margin of safety or dosage "window" with a dose of 1400 mg of microspheres required to achieve an Fe load with the low range of hepatic Fe toxicity of 1 mg Fe/g liver wet weight. A 250 fold overdosage is necessary to load the liver with 10 mg Fe/g wet weight which is often seen in symptomatic transfusional hemosiderosis (range 1-10 mg/g liver wet weight).

B. Paramagnetic Properties.

$Fe+3$ is a potent paramagnetic with 5 unpaired electrons and a magnetic moment of 5.9 (Bohr magnetons). An increase in $T_2$ relaxivity ($R_2$) in particulate bound form of paramagnetic material such as iron (i.e., methemoglobin, hemosiderin, etc.) has been observed. A pathophysiologic model of this phenomena is seen in transfusional hemosiderosis and chronic parenchymal hemorrhage. However, the $T_2$ relaxivity seen with magnetite-albumin microspheres far exceeds the apparent paramagnetic/ferromagnetic properties of hemosiderin based on total Fe load necessary to achieve calculated $T_1$ and $T_2$ values. The reason for this is not known with certainty. Possibly the maximum peripheral and central dispersion of magnetite in the albumin matrix results in maximum generation of microfield inhomogeneity. The diminution in $T_2$ probably represents largely a $T_2^*$ effect. In addition, the enhanced $T_2$ effect of iron (Fe) in the form of magnetite is probably due to the ferromagnetic and/or superparamagnetic properties of iron. The effect of the magnetic particles is that abnormal tissues become intense (relative increase in signal intensity) relative to normal tissue because of the action of the iron compound on normal tissue. This is advantageous since hot spot imaging of abnormalities is usually preferable to cold spot imaging.

I claim:

1. The method of imaging a tumor in the liver or spleen of a human subject, comprising:
   (a) parenterally administering to the human subject prior to magnetic resonance imaging (MRI) examination an aqueous suspension composed essentially of 1.5 to 8 micron diameter microspheres, said microspheres having a biodegradeable matrix with a contrast agent dispersed therein selected from the group consisting of paramagnetic and ferromagnetic contrast agents, the quantity of said microspheres administered being effective to appreciably reduce the $T_2$ relaxation time of the subject's liver and/or spleen;
   (b) delaying the examination until the microspheres have been segregated by the reticuloendothelial system and are concentrated in the liver and spleen; and then
   (c) carrying out an MRI examinaiton of the liver and/or spleen by $T_2$ imaging or mixed $T_1$ and $T_2$ imaging to obtain an image in which the normal liver or spleen tissues appear dark and the tumor appears light with distinct margins therebetween.

2. The method of claim 1 in which the micropsheres have an average size range of from 2 to 5 microns diameter.

3. The method of claim 1 in which said contrast agent is in the form of ferromagnetic particles having superparamagnetic properties.

4. The method of claim 1 in which said contrast agent is in a chelated water-soluble form.

5. The method of claim 1 in which said contrast agent is a ferromagnetic compound in the form of particles sized from 50 to 300 Angstroms.

6. The method of claim 5 in which said ferrogmagnetic compound is magnetite.

7. The method of imaging a tumor in the liver or spleen of a human subject, comprising:
   (a) intravenously administering to the human subject prior to magnetic resonance imaging (MRI) examination an aqeuous suspension composed essentially of microspheres having an average size of from 2 to 5 microns diameter, said microspheres being composed of a biodegradable matrix having a ferromagnetic contrast agent dispersed therein, the quantity of said microspheres administered being effective to appreciably reduce the $T_2$ relaxation time of the subject's liver and/or spleen;
   (b) delaying the examination until the microspheres have been segregated by the reticuloendothelial system and are concentrated in the liver and spleen; and then
   (c) carrying out an MRI examination of the liver and/or spleen by $T_2$ imaging or mixed $T_1$ and $T_2$ imaging to obtain an image in which the normal liver or spleen tissues appear dark and the tumor appears light with distinct margins therebetween.

8. The method of claim 7 in which said ferromagnetic contrast agent is in the form of particles having superparamagnetic properties.

9. The method of claim 7 in which said ferromagnetic contrast agent is in a chelated water-soluble form.

10. The method of claim 7 in which said ferromagnetic contrast agent is in the form of particles sized from 50 to 300 Angstroms.

11. The method of claim 10 in which said ferromagnetic contrast agent is magnetite.

12. The method of imaging a tumor in the liver or spleen of a human subject, comprising:
    (a) intravenously administering to the human subject prior to magnetic resonance imaging (MRI) examination an aqueous suspension composed essentially of 1.5 to 8 micron diameter microspheres, said microspheres having a matrix of human serum albumin with magnetite particles dispersed therein, the quantity of said micropsheres administered being effective to appreciably reduce the $T_2$ relaxation time of the subject's liver and/or spleen;
    (b) delaying the examination until the microspheres have been segregated by the reticuloendothelial system and are concentrated in the liver and spleen; and then
    (c) carrying out an MRI examination of the liver and/or spleen by $T_2$ imaging or mixed $T_1$ and $T_2$ imaging to obtain an image in which the normal liver or spleen tissues appear dark and the tumor appears light with distinct margins therebetween.

13. The method of claim 12 in which the microspheres have an average size of from 2 to 5 microns diameter, and said magnetite particles are sized from 50 to 300 Angstroms and have superparamagnetic properties.

14. The method of claim 12 in which said microspheres have an average size of from 2 to 5 microns diameter and contain from 10 to 40 parts by weight of said magnetite particles per 100 parts of sid albumin, said particles being sized from 50 to 300 Angstroms and having superparamagnetic properties, the quantity of said microspheres administered ranging from 1 to 40 milligrams per kilogram of body weight.

* * * * *